(12) United States Patent
van Es et al.

(10) Patent No.: US 10,214,474 B2
(45) Date of Patent: Feb. 26, 2019

(54) OXIDATION OF URONIC ACIDS TO ALDARIC ACIDS

(71) Applicant: COOPERATIE KONINKLIJKE COSUN U.A., Breda (NL)

(72) Inventors: Daniël Stephan van Es, Bennekom (NL); Rajeesh Kumar Pazhavelikkakath Purushothaman, Wageningen (NL); Augustinus Emmanuel Frissen, Wageningen (NL); Jacobus van Haveren, Ede (NL); Frits van der Klis, Sliedrecht (NL)

(73) Assignee: COOPERATIE KONINKLIJKE COSUN U.A., Breda (NL)

( * ) Notice: Subject to any disclaimer, the term of this patent is extended or adjusted under 35 U.S.C. 154(b) by 0 days.

(21) Appl. No.: 15/516,998

(22) PCT Filed: Oct. 6, 2015

(86) PCT No.: PCT/NL2015/050703
§ 371 (c)(1),
(2) Date: Apr. 5, 2017

(87) PCT Pub. No.: WO2016/056907
PCT Pub. Date: Apr. 14, 2016

(65) Prior Publication Data
US 2017/0305829 A1    Oct. 26, 2017

(30) Foreign Application Priority Data

Oct. 6, 2014  (EP) ..................................... 14187763

(51) Int. Cl.
*C07C 51/235*  (2006.01)
*B01J 23/52*   (2006.01)
(Continued)

(52) U.S. Cl.
CPC ............. *C07C 51/235* (2013.01); *B01J 23/52* (2013.01); *B01J 23/66* (2013.01); *B01J 37/0211* (2013.01);
(Continued)

(58) Field of Classification Search
CPC  C07C 51/235; C07C 1/00; B01J 23/52; B01J 23/66; B01J 21/04; B01J 21/063; C07H 7/00; C07H 7/033
See application file for complete search history.

(56) References Cited

U.S. PATENT DOCUMENTS

2011/0306790 A1    12/2011  Murphy et al.
2016/0090346 A1*    3/2016  Diamond ........... B01D 15/1821
                                                              562/580

FOREIGN PATENT DOCUMENTS

WO    2005003072 A1    1/2005
WO    2013151428 A1   10/2013

OTHER PUBLICATIONS

Gupta, Kalyan Kali Sen, et al. Reactivity of some sugars and sugar phosphates towards gold(III) in sodium acetate-acetic acid buffer medium, Carbohydrate Research, vol. 330, pp. 115-123, 2001.
(Continued)

*Primary Examiner* — Yate' K Cutliff
(74) *Attorney, Agent, or Firm* — McDermott Will & Emery LLP

(57) ABSTRACT

Disclosed is the oxidation of uronic acids, such as galacturonic acid, to the corresponding aldaric acids, such as galactaric acid, under neutral or acidic conditions. Use is made of a supported gold catalyst. The oxidation occurs in good selectivity and yield, under unexpectedly mild conditions. A source of galacturonic acids is pectins, such as from sugar beet pulp.

13 Claims, 1 Drawing Sheet

(51) Int. Cl.
  *B01J 23/66* (2006.01)
  *C07H 7/033* (2006.01)
  *B01J 37/02* (2006.01)
  *C07C 51/31* (2006.01)
  *C07C 59/285* (2006.01)
  *B01J 37/18* (2006.01)

(52) U.S. Cl.
  CPC .......... *C07C 51/313* (2013.01); *C07C 59/285* (2013.01); *C07H 7/033* (2013.01); *B01J 37/024* (2013.01); *B01J 37/18* (2013.01)

(56) References Cited

OTHER PUBLICATIONS

Biella, Serena, et al. Selective Oxidation of D-Glucose on Gold Catalyst, Journal of Catalysis, vol. 206, pp. 242-247, 2002.
International Search Report and Written Opinion dated Mar. 31, 2016 in PCT Application No. PCT/NL2015/050703.

* cited by examiner

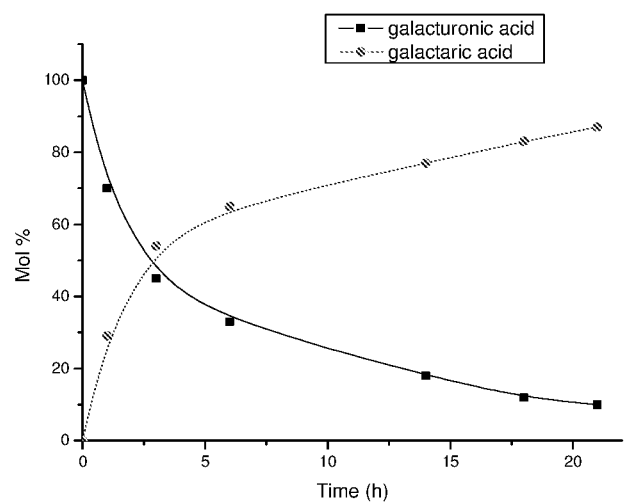

OXIDATION OF URONIC ACIDS TO ALDARIC ACIDS

RELATED APPLICATIONS

This application is a United States National Phase under 35 U.S.C. § 371 of International Application No. PCT/NL2015/050703, filed on Oct. 6, 2015, which claims the benefit of European Patent Application No. 14187763.9, filed on Oct. 6, 2014, both of which are hereby incorporated by reference in their entirety.

FIELD OF THE INVENTION

The invention pertains to the synthesis of aldaric acids and derivatives thereof, from uronic acids under base-free circumstances. Also, the invention pertains to a method of producing galactaric acid from sugar beet pulp.

BACKGROUND OF THE INVENTION

Aldaric acids are a group of sugar acids, where the terminal hydroxyl or aldehyde groups of the sugars have been replaced by terminal carboxylic acids. These acids are characterized by the formula HOOC—(CHOH)n-COOH, with n being an integer of from 1 to 5. These dicarboxylic acids, on account of their combined functionalities, are interesting chemicals. E.g., as sequestering agents, corrosion inhibitors or monomers for making polymers made on the basis of dicarboxylic acids, such as polyesters or polyamides. Preferred aldaric acids are those wherein n is an integer of from 3 to 5. Aldaric acids of particular interest are those derived from C5 and C6 sugars, like xylaric acid, glucaric acid, mannaric acid, gularic acid and idaric acid. An aldaric acid of particular interest is galactaric acid, the aldaric acid corresponding to the sugar galactose. Applications for galactaric acid range from sequestering agents (Kohn et al. Collect. Czech. Chem. Commun. 1986, 1150) to building blocks for polymers (e.g. Moore & Bunting Polym. Sci. Technol., Adv. Polym. Synth., 51). Other aldaric acids of particular interest are glucaric acid, mannaric acid and gularic acid, aldaric acids that can be obtained from the carbohydrate fraction of biomass sources including pectins and a variety of different seaweeds.

In WO 2013/151428 a method is disclosed to produce aldaric acids by the oxidation of the corresponding uronic acid, wherein a starting material comprising the uronic acid is subjected to oxygen under the influence of a supported gold catalyst and in the presence of a base. An interesting aspect of this method, is that it makes it possible to unlock the chemical potential present in the form of uronic acids in hemicellulosic streams, which are typically obtainable from biorefineries.

Biorefineries serve to conduct the sustainable processing of biomass into a spectrum of marketable biobased products and bioenergy. A biorefinery is an installation that can process biomass into multiple products using an array of processing technologies. In general, biomass coming from plants, will result in streams based on lignin, cellulose, and hemicellulose, respectively. Hemicelluloses can be removed from biomass, e.g. by treatment with hot pressurized water. This results in formation of water soluble oligomeric and monomeric sugars and their dehydration products such as furfural and hydroxymethyl furfural. Another source of hemicelluloses is in the agro-food industry. Whilst hemicelluloses, in theory, are a source of a wide variety of useful chemicals, it is desired to find methods to make better use of this potential, by providing economically attractive processes to harvest such chemicals therefrom. A particular interesting hemicellulosic feedstock from the agro-food industry comprises sugar beet pulp, a by-product of the sugar beet industry. Sugar beet pulp contains a high content of pectic substances, being composed of arabinose and galacturonic acid as the main monomers. Other sources of pectins are all kinds of different fruits, including e.g. apples, carrots, cherries and citrus fruits, especially citrus peels. Another potential source of uronic acids is being formed by alginates. A large variety of seaweeds including red and brown seaweeds like *Laminaria digitata, Saccharina latissima* and *Ulva lactuca* contain huge amounts of alginates being composed of mannuronic acid and guluronic acid as the composing monomers; after hydrolysis of the alginates such monomers can be used as feedstock for the production of aldaric acids.

Whilst the process disclosed in the aforementioned reference is highly suitable, it would be desired to be able to convert the uronic acids under acidic, rather than basic circumstances. This would bring about a substantial advantage in that the stream of raw materials by nature is neutral to acidic, so that the addition of large amounts of base can be dispensed with. Also, the desired end-products, viz. aldaric acids, can only be isolated as a free acid by ultimately adjusting the pH to acidic. Thus, a process in which the whole oxidative conversion would take place under acidic conditions, would avoid both the use of additional base and the generation of a relatively large amount of salts as a by-product of ultimately acidifying the reaction product, so as to isolate the free aldaric acid.

SUMMARY OF THE INVENTION

In order to address one or more of the foregoing desires, the invention, in one aspect, provides a process for the preparation of an aldaric acid by the oxidation of the corresponding uronic acid, wherein a starting material comprising the uronic acid is subjected to oxygen under the influence of a supported gold catalyst at a pH below 7.

In another aspect, the invention presents the use of a uronic acid as a starting material for the production of the corresponding aldaric acid, wherein the uronic acid is subjected to oxygen under the influence of a supported monometallic or bimetallic gold catalyst, at a pH below 7.

BRIEF DESCRIPTION OF THE DRAWINGS

FIG. 1 displays the conversion of galacturonic acid in the presence of $Au/Al_2O_3$ is shown as a function of time.

DETAILED DESCRIPTION OF THE INVENTION

In a broad sense, the invention is based on the unexpected finding that, in putting to use the versatile chemical potential available of bio-based uronic acids by catalytic oxidation, no basic conditions need to be created. These bio-based uronic acids are available in, e.g., hemicellulosic and pectin rich waste streams or seaweeds.

To this end, the inventors have judiciously identified supported gold catalysts to catalyse the oxidation, whilst conducting the oxidation at a neutral to acidic pH. The gold catalyst can be a monometallic or bimetallic gold catalyst. In the former case, gold is the only catalytically active metal present. In the latter case, the gold is present together with a metal from the platinum group of metals, viz. selected from the group consisting of palladium, platinum, rhodium, ruthenium, iridium and osmium. Therein the molar ratio of gold to the other metal will generally range from 9.5:0.5 to 2:8. Throughout this description, the term "gold catalyst" is used to refer to the aforementioned monometallic or bimetallic gold catalyst, with monometallic gold catalysts being preferred.

The starting material for the catalytic oxidation of the invention can be the uronic acid itself. Preferred uronic acids include: galacturonic acid, glucuronic acid, mannuronic acid, iduronic acid, guluronic acid and most preferably galacturonic acid. The invention provides an efficient, and highly selective catalytic oxidation of the uronic acid to the corresponding aldaric acid, e.g. from galacturonic acid to galactaric acid. To this end, supported gold catalysts are used. Such catalyst comprise support of a metal oxide, e.g. $TiO_2$ or $Al_2O_3$, or other materials customary in the art of providing supported catalysts for heterogeneous catalysis.

The metal oxide support generally is a catalyst support made of at least one oxide of a main group or transition metal or metalloid, including compounds which comprise more than one metal and/or metalloid. Preference is given in this connection to oxides of metals or metalloids of main group 2 of the Periodic Table, such as MgO, CaO or BaO, oxides of metals or metalloids of main group 3 of the Periodic Table, such as $Al_2O_3$ or lanthanoid oxides or oxides of metals or metalloids of main group 4 (IVA or IVB) of the Periodic Table, such as $TiO_2$, $ZrO_2$, $SnO_2$, or $SiO_2$. Also $Fe_2O_3$ can be employed. The compounds having more than one metal and/or metalloid are preferably silicates, especially aluminosilicates. The gold comprises metallic gold, dispersed onto the support, preferably as nanoparticles.

As an alternative for the metal oxide supports, the gold can be supported on carbon supports, e.g. activated carbons, carbon blacks, graphites, carbon nanotubes, carbon nanofibers, etc.

The support will generally comprise, in weight percentages relative to the support, of from 0.1% to 5% gold. In an interesting embodiment, the percentages are 0.5% to 1.5%. In another interesting embodiment, the percentages are 2% to 4%. The metal oxide-supported gold catalyst is preferably employed in the form of a powder or granules.

The gold nanoparticles generally have a diameter of below 10 nm, preferably of below 6 nm and most preferably of from 1 to 3 nm. The metal oxide-supported gold catalysts used according to the invention can be prepared, i.e. gold can be deposited in the form of nanoparticles on the metal oxide support materials, for example by employing precipitation methods where the gold is deposited in the form of oxidic/hydroxic gold precursors by precipitation on the metal oxide support, or is precipitated together with a precursor of the metal oxide support. Gold can also be introduced in the sol-gel synthesis of the support, for example of an earth metal oxide or a transition metal oxide. Also known are impregnation with gold solutions and the application of gold colloids to supports using various polymers as colloid stabilizers. Suitable methods for preparing metal oxide-supported gold catalysts include for example precipitation methods, deposition-precipitation methods and methods for chemical deposition from the gas phase (CVD methods) and are described inter alia in Prati and Martra, Gold Bulletin, 32(3) (1999), 96-101; Wolf and Schuth, Applied Catalysis A: General., 226 (2002), 1-13, and Berndt et al., Applied Catalysis A: General, 6442 (2003), 1-11.

The uronic acid is subjected to oxygen in order to affect the oxidation. Whilst the oxygen can be in the form of air, it is preferred that the catalytic oxidation is conducted under the influence of an oxygen-containing gas-stream comprising at least 40% oxygen, preferably at least 60% oxygen. More preferably, the oxygen-containing gas-stream is oxygen having a purity of from 90%-100%. An advantage of the invention, is that it also works well with relatively cheap compressed air.

The oxidation can be conducted under relatively mild conditions. Preferred temperatures range from 20° C. to 100° C. (293K-373K), preferably from 30° C. to 80° C., more preferably from 40° C. to 70° C., and most preferred from 50° C. to 60° C.

The oxidation is conducted for a suitable period of time, generally more than 0.5 hours and less than 48 hours. In an interesting embodiment, the time is 6-30 hours, preferably 18-24 hours. In another interesting embodiment, the time is 36 to 48 hours.

The pH during the oxidation is neutral to acidic, generally above 0 and below 7. Although an adjustment of the pH within this range is conceivable, it is preferred that the process is conducted in the absence of a base. Preferably the pH is 0.5 to 6.5, more preferably 1-6, and most preferably 1-4. In a particularly interesting embodiment, the pH is not affected by the addition of acid or base, but is the pH naturally occurring during the reaction. Thus, the pH is given by the natural pH of the substrate (i.e. the uronic acid) and, increasingly as the reaction proceeds, the natural pH of the formed aldaric acid. A typical range for the pH in this event is of from 2 to 3.5. A clear advantage, and a surprising finding, is thus that the reaction can be conducted without any measures of pH adjustment. In another interesting embodiment, the substrate is a hydrolysate of pectin or alginate obtained by enzymatic hydrolysis pre-treatment. This product stream contains besides the uronic acid also other acidic compounds such as formic acid, acetic acid, and the like. An advantage is that the so obtained acidic product stream needs significantly less further downstream processing. A typical range for the pH in this event is of from 1 to 3.

The method of the invention is generally conducted at atmospheric pressure, although other pressures (range 1-10 bar) can also be employed.

The invention preferably pertains to a process for the preparation of galactaric acid by the oxidation of galacturonic acid using the above-described method using a supported gold catalyst. By further preference the galacturonic acid is isolated from an agro residue stream comprising pectin hydrolyzates.

In this respect, the invention also pertains to the catalytic oxidation of pectin-constituents (galacturonic acid and arabinose) to aldaric acids (galactaric acid) and aldonic acids (arabinonic acid) with molecular oxygen or air, using supported gold catalysts, under neutral to acidic conditions as mentioned above.

The process of the invention can be conducted in a manner generally known to the skilled person, in such reactors as can normally be used for other catalytic oxidation processes.

The aldaric acids produced can be further worked up (separated, purified) using techniques generally known in the art. An advantage of the invention is that no acid needs to be added in order to isolate the desired end-products, viz. aldaric acids, as a free acid, thus also avoiding the formation of salts as by-products.

In summary, the invention provides the oxidation of uronic acids, such as galacturonic acid, to the corresponding aldaric acids, such as galactaric acids. Use is made of a supported gold catalyst as defined hereinbefore. The oxidation occurs in good selectivity and yield, under unexpectedly possible neutral to acidic conditions. A source of galacturonic acids is pectins, such as from sugar beet pulp.

By virtue of the process of the invention, the invention opens up the use, and particularly in a more economical or beneficial manner, of various biobased starting materials for the production of various desired chemicals.

Thus, in one aspect, the invention includes the use of uronic acids as a starting material for the production of an aldaric acid, wherein the uronic acid is subjected to oxygen under the influence of a supported gold catalyst, at a pH below 7, preferably in the absence of a base. Preferred pH ranges are discussed above.

In another aspect, the invention includes the use of sugar beet pulp or citrus fruits as a starting material for the oxidation of galacturonic acid into galactaric acid, or glucuronic acid into glucaric acid, by subjecting said starting materials to oxygen under the influence of a supported gold catalyst, at a pH below 7, preferably in the absence of a base. Preferred pH ranges are discussed above.

In yet another aspect, the invention provides the use of seaweeds as a starting material for the oxidation of mannuronic acid and guluronic acid into mannaric acid and gularic acid, by subjecting said starting material to oxygen under the influence of a supported gold catalyst, at a pH below 7, preferably in the absence of a base. Preferred pH ranges are discussed above.

The invention also presents a novel use for supported gold catalysts. Accordingly, in this aspect of the invention, the use is presented of a supported gold catalyst for the oxidation of a starting material selected from the group consisting of uronic acid, pectin hydrolyzates, sugar beet pulp, citrus fruits, and seaweeds. In this use, the starting material is subjected to oxygen under the influence of said supported gold catalyst at a pH below 7, preferably in the absence of a base. Preferred pH ranges are discussed above.

Preferably, the aforementioned uses of various starting materials, and the novel use of supported gold catalysts, are realized by carrying out the oxidation by a process according to any of the embodiments described hereinbefore.

The invention will be illustrated hereinafter with reference to the following non-limiting examples. Percentages are indicated by weight.

General Procedure

The base free oxidation of galacturonic acid to galactaric acid was performed in a 75 mL batch reactor set-up (Parr Series 5000 Multiple Reactor System). The reactions were typically carried out in water at a temperature of 333K and an oxygen pressure of 3 bar in base free conditions. The galacturonic acid to metal intake was set at 448 mol/mol. Firstly, the reactor was charged with galacturonic acid (2 mmol) in 20 mL of deionised water. Subsequently the catalyst was added and the autoclave was closed, flushed and finally pressurised to 3 bar oxygen. The reactor contents were heated under stirring using magnetic stirring bars (700 rpm).

Materials

Au/$TiO_2$ (1 wt %), Au/$Al_2O_3$ (1 wt %) and Au/ZnO, (1.0 wt %), all with Au particle dimensions between 2 and 3 nm, were supplied by Strem-Autek. Pt/C (1 wt %) and Rh/C (wt %) were obtained from Sigma-Aldrich. Pd/C (1 wt %) and Pt/$Al_2O_3$ (1 wt %) were procured from Alfa-Aesar. Ru/$Al_2O_3$ (0.5 wt %) and Ru/C (5 wt %) were obtained from Strem chemicals. D-(+)-Galacturonic acid monohydrate (≥97%) and galactaric acid (97%) were purchased from Sigma-Aldrich. Oxygen (99.995%) was obtained from Linde Gas Benelux B.V., The Netherlands. $TiO_2$ (Evonik, P25, >99.5%), γ-$Al_2O_3$ (Saint Gobain Norpro, surface area 254 m$^2$/g), ZnO (Zinc oxide AC45, Brüggemann Chemical Heilbronn) and activated carbon (Norit, SX1G) were received as gift.

Product Analysis by HPLC

Galacturonic acid concentrations were determined by HPLC analysis after separating the catalyst. Prior to galactaric acid analysis, the pH of the reaction mixture was adjusted to 12 so as to ensure complete dissolution followed by the quick separation of the catalyst. In a typical analysis 200 μL of the sample was transferred to an HPLC vial and diluted to 500 μL with the eluent (3 mM $H_2SO_4$). An injection volume of 10 μL was used for each analysis. The samples were analysed on a Waters HPLC instrument equipped with an Alltech IOA-100 column maintained at 90° C. using $H_2SO_4$ (3 mM) in milli-Q water as the eluent with a flow rate of 0.4 mL/min. The analytes were identified using an RI (refractive index) detector (Waters) by comparison with authentic samples. Concentrations were determined using calibration curves obtained by injecting standard solutions of known concentrations. Conversion and selectivity of components are calculated on the basis of carbon mass.

Catalyst Synthesis

Au/C

Monometallic gold on carbon catalyst was prepared by a sol immobilisation method described in literature (F. Porta and L. Prati, Journal of Catalysis, 2004, 224, 397-403; R. G. DiScipio, Analytical Biochemistry, 1996, 236, 168-170; L. Prati and G. Martra, Gold Bulletin, 1999, 32, 96-101.) In a typical procedure, $HAuCl_4.3H_2O$ (0.071 mmol) was dissolved in 300 mL of milli-Q water containing polyvinylalcohol (PVA, 2 wt % solution, 3.8 mL) as the protecting agent. Subsequently $NaBH_4$ (0.28 mmol in 3 mL of milli-Q water) was added to the solution under vigorous magnetic stirring. The pH of the colloid was adjusted to 2.3 using 0.2 M $H_2SO_4$. Within 5 minute of sol generation the carbon support (2 g) was added and stirred vigorously for 2 h. The catalyst was separated by filtration and washed exhaustively with deionised water. Finally, the catalyst was dried at 110° C. in static air for 24 h. The catalyst is designated as Au/C.

Au—Pt/C

The Au/C was suspended in 240 mL of milli-Q water containing $K_2PtCl_4$ (0.013 g) and PVA (0.45 mL, 2 wt % solution). Hydrogen gas was bubbled through this slurry using an ace gas dispersion tube at a flow rate of 100 mL/min at atmospheric pressure and at room temperature for 3 h. The slurry was stirred for additional 16 h. The catalyst was separated by filtration, washed thoroughly with deionised water and finally dried at 110° C. in static air for 24 h. The catalyst is designated as Au—Pt/C.

Example 1

Oxidation of Galacturonic Acid in Water Using Noble Metals on Oxidic Supports in the Absence of Base The oxidation reactions of galacturonic acid to galactaric acid were carried out at 333K using molecular oxygen (3 bar) as the oxidising agent. A number of Au, Pt and Pd catalysts on various supports were screened. The results obtained are summarised in Table 1 (metal oxide supports) and 2 (carbon supports).

The results obtained for the base free oxidation of galacturonic acid (GALUA) using various noble metals on oxidic supports are summarised in Table 1. When using Au/$TiO_2$ as the catalyst at room temperature under base free conditions, no galacturonic acid conversion was observed (Table 1, entry 1). When the temperature was raised to 333K, Au/$TiO_2$ gave 45% galacturonic acid conversion after 3 h (Table 1, entry 2) The main product obtained was galactaric acid (98%). When the oxidation was performed for 21 h at 333K, the conversion reached 67% with 94% galactaric acid (Table 1, entry 3). The by-products were glycolic acid (2%), oxalic acid (2%) and formic acid (1%).

TABLE 1

Oxidation of galacturonic acid over noble metals on oxidic supports [a]

| Entry | Catalyst | Time (h) | Temp. K | Galacturonic acid conv. % | Galactaric acid sel. % |
|---|---|---|---|---|---|
| 1 | 1 wt % Au/TiO$_2$ | 3 | RT | 0 | — |
| 2 | 1 wt % Au/TiO$_2$ | 3 | 333 | 45 | 98 |
| 3 | 1 wt % Au/TiO$_2$ | 21 | 333 | 67 | 94 |
| 4 | 1 wt % Au/ZnO | 21 | 333 | 70 | 93 |
| 5 | 1 wt % Au/Al$_2$O$_3$ | 21 | RT | 0 | — |
| 6 | 1 wt % Au/Al$_2$O$_3$ | 21 | 303 | 20 | 99 |
| 7 | 1 wt % Au/Al$_2$O$_3$ | 21 | 313 | 45 | 96 |
| 8 | 1 wt % Au/Al$_2$O$_3$ | 21 | 323 | 68 | 95 |
| 9 | 1 wt % Au/Al$_2$O$_3$ | 21 | 333 | 87 | 94 |
| 10 | 1 wt % Au/Al$_2$O$_3$ | 21 | 373 | 100 | 50 |
| 11 | 1 wt % Pt/Al$_2$O$_3$ | 21 | 333 | 1.5 | 72 |
| 12 | 1 wt % Pd/Al$_2$O$_3$ | 21 | 333 | 1 | 99 |
| 13 | 0.5 wt % Ru/Al$_2$O$_3$ | 21 | 333 | 3 | 98 |
| 14 | TiO$_2$ | 21 | 333 | 0 | — |
| 15 | ZnO | 21 | 333 | 0 | — |
| 16 | Al$_2$O$_3$ | 21 | 333 | 0 | — |

[a] Reaction conditions: 2 mmol of galacturonic acid in 20 mL of deionised water, p(O$_2$) = 3 bar, stirring speed = 700 rpm, galacturonic acid/(bulk)metal = 448 mol/mol, initial pH = 2.64.

When using Au/ZnO as the catalyst for the base free oxidation of GALUA, a 70% conversion with 93% galactaric acid selectivity was obtained (Table 1, entry 4). The by-products are oxalic acid (3.5%), glycolic acid (1%) and formic acid (1%).

When the oxidation reaction was performed over Au/Al$_2$O$_3$ as the catalyst, higher galacturonic acid conversion (87%) was obtained with 94% galactaric acid selectivity at 333K. The by-products identified were glycolic acid (1%), oxalic acid (3.5%) and formic acid (0.5%) (Table 1, entry 9). The influence of temperature on the conversion and selectivity for this catalyst is shown in Table 1, entries 5-10: At room temperature no conversion is observed, while at 303K 20% conversion is achieved with complete selectivity. With increasing temperatures the conversion increases further (up to 100% at 373K), with decreasing selectivities (50% at 373K, Table 1 entry 10). For the reaction at 373K the following side products identified: oxalic acid (5%), glycolic acid (3%), lactic acid (1%), glyceric acid (1%), acetic acid (3%).

Additional catalyst experiments were performed using three other Al$_2$O$_3$ supported catalysts namely Pt/Al$_2$O$_3$, Pd/Al$_2$O$_3$, and Ru/Al$_2$O$_3$ (Table 1, entries 11-13). Catalytic performances of these catalysts were very low, indicating the specificity of Au catalysts for the oxidation of uronic acids.

The bare supports (TiO$_2$, Al$_2$O$_3$ and ZnO) did not give any galacturonic acid conversion (Table 1, entries 14-16) under comparable reaction conditions.

In FIG. 1 the conversion of galacturonic acid in the presence of Au/Al$_2$O$_3$ is shown as a function of time.

Example 2

Oxidation of Galacturonic Acid in Water Using Noble Metals on Carbon Supports in the Absence of Base In Table 2, the catalytic results on carbon supported noble metal catalysts for the base free oxidation of galacturonic acid are provided. The activity of Au/C (56% conversion, 100% selectivity) is comparable to the results obtained with Au on metal oxides (Example 1). However, while Pt/Al$_2$O$_3$ showed only very limited conversion (1.5%), the Pt/C catalyst gave 26% conversion with almost complete selectivity (Table 2, entry 2). For the other carbon supported metals (Pd, Ru, Rh), only Pd showed 7% conversion (Table 2, entries 3-5) while the other catalysts were inactive. Activated carbon itself (Table 2, entry 7) was also inactive.

A bimetallic catalyst, 0.7 wt % Au, 0.3 wt % Pt/C showed 100% selectivity for galactaric acid at 65% conversion of galacturonic acid.

TABLE 2

Oxidation of galacturonic acid in water using carbon supported noble metals in the absence of base.

| Entry | Catalyst | Galacturonic acid conv. % | Galactaric acid sel. % |
|---|---|---|---|
| 1 | 0.7 wt % Au/C | 56 | 100 |
| 2 | 1 wt % Pt/C | 26 | 99 |
| 3 | 1 wt % Pd/C | 7 | 99 |
| 4 | 5 wt % Ru/C | 0 | — |
| 5 | 5 wt % Rh/C | 0 | — |
| 6 | 0.7 wt % Au; 0.3 wt % Pt/C | 65 | 100 |
| 7 | Carbon | 0 | — |

[a] Reaction conditions: 2 mmol of galacturonic acid in 20 mL of deionised water, p(O$_2$) = 3 bar, stirring speed = 700 rpm, galacturonic acid/(bulk)metal = 448 mol/mol, initial pH = 2.64, Time = 21 h, Temp. = 333 K Example 3

Stability of Galactaric Acid

In order to investigate the stability of galactaric acid, experiments were performed in which galactaric acid in water was subjected to standard oxidation reaction conditions (333K, 3 bar oxygen) over Au/TiO$_2$ and Au/Al$_2$O$_3$. After 21 h, no galactaric acid conversion was observed, indicating the excellent stability of the desired product under the given reaction conditions. However, when the temperature was increased to 373K in the presence of Au/Al$_2$O$_3$, 60% conversion of galactaric acid was observed. The following by-products were identified: oxalic acid (5%), glycolic acid (9.5%), lactic acid (1%) and acetic acid (4.5%). The results are summarized in Table 4.

TABLE 3

Stability of galactaric acid under reaction conditions[a]

| Entry | Catalyst | Time (h) | Temp. K | Galactaric acid conv. % |
|---|---|---|---|---|
| 1 | 1 wt % Au/TiO$_2$ | 21 | 333 | 0 |
| 2 | 1 wt % Au/Al$_2$O$_3$ | 21 | 333 | 0 |
| 3 | 1 wt % Au/Al$_2$O$_3$ | 26 | 373 | 60 |

[a] Reaction conditions: 2 mmol of galactaric acid in 20 mL of deionised water, p(O$_2$) = 3 bar, stirring speed = 700 rpm, galactaric acid/(bulk)metal = 448 mol/mol.

The invention claimed is:

1. A process for the preparation of an aldaric acid by the oxidation of the corresponding uronic acid, wherein a starting material comprising the uronic acid is subjected to oxygen under the influence of a supported gold catalyst at a pH in a range of from 1-6, wherein the gold catalyst is a monometallic or bimetallic gold catalyst, wherein the oxidation of the corresponding uronic acid is carried out at a temperature in the range of from 30° C. to 100° C.

2. A process according to claim 1, wherein the gold catalyst is a bimetallic gold catalyst comprising gold and a metal selected from the group consisting of palladium, platinum, rhodium, ruthenium, iridium and osmium.

3. A process according to claim 1, wherein the pH is in a range of from 1-4.

4. A process according to claim 1, wherein the pH is the pH naturally occurring during the reaction.

5. A process according to claim 1, wherein the oxygen is in the form of air, or in the form of an oxygen-containing gas-stream, comprising at least 40% oxygen.

6. A process according to claim 1, wherein the uronic acid is selected from the group consisting of galacturonic acid, glucuronic acid, mannuronic acid, guluronic acid, and mixtures thereof.

7. A process according to claim 6, wherein the starting material comprises a pectin hydrolyzate.

8. A process according to claim 1, followed by the purification of the aldaric acid.

9. A process according to claim 1, wherein the aldaric acid is selected from the group consisting of galactaric acid, xylaric acid, glucaric acid, mannaric acid, gularic acid and idaric acid.

10. A process according to claim 5, wherein the oxygen-containing gas-stream is oxygen-enriched air.

11. A process according to claim 5, wherein the oxygen-containing gas-stream comprises at least 60% oxygen.

12. A process according to claim 6, wherein the starting material is sourced from sugar beet pulp.

13. A process according to claim 1, wherein the oxidation is carried out at a temperature in the range of from 40° C. to 70° C.

* * * * *